(12) United States Patent
Cangialosi (10) Patent No.: US 7,824,369 B2
(45) Date of Patent: Nov. 2, 2010

(54) BALLOON CATHETER HAVING OSMOTIC INFLATION SYSTEM

(75) Inventor: Vincent J. Cangialosi, Beverly, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1036 days.

(21) Appl. No.: 11/111,233

(22) Filed: Apr. 21, 2005

(65) Prior Publication Data

US 2006/0253147 A1 Nov. 9, 2006

(51) Int. Cl.
*A61M 29/00* (2006.01)
*A61M 25/00* (2006.01)
*A61B 5/00* (2006.01)

(52) U.S. Cl. .............. 604/96.01; 600/585; 604/97.01; 604/99.01; 604/915; 604/920

(58) Field of Classification Search ............. 604/97.01, 604/96.01, 102.01, 892.1, 31, 523, 93.01, 604/98.01, 99.01, 82, 99.02, 915, 920, 99.04; 606/192
See application file for complete search history.

(56) References Cited

U.S. PATENT DOCUMENTS

| | | | | |
|---|---|---|---|---|
| 3,087,492 A | * | 4/1963 | Chester et al. ............. | 604/99.02 |
| 3,818,903 A | * | 6/1974 | Bleecker ................... | 604/98.01 |
| 3,880,164 A | * | 4/1975 | Stepno ....................... | 604/131 |
| 4,245,639 A | * | 1/1981 | La Rosa .................... | 604/97.02 |
| 4,327,734 A | | 5/1982 | White, Jr. | |
| 5,492,532 A | * | 2/1996 | Ryan et al. ................ | 604/103.09 |
| 5,634,892 A | * | 6/1997 | Whalen ..................... | 604/6.14 |
| 6,241,727 B1 | * | 6/2001 | Tu et al. ..................... | 606/41 |
| 6,245,008 B1 | * | 6/2001 | Leschinsky et al. ....... | 600/18 |
| 6,544,208 B2 | * | 4/2003 | Ethier et al. ............... | 604/8 |
| 6,656,151 B1 | | 12/2003 | Blatter | |
| 2005/0096750 A1 | * | 5/2005 | Kagan et al. .............. | 623/23.65 |
| 2005/0261726 A1 | * | 11/2005 | Pile-Spellman ............ | 606/200 |

* cited by examiner

*Primary Examiner*—Kevin C Sirmons
*Assistant Examiner*—Shefali D Patel (57) ABSTRACT

A system and method for inflating and deflating a catheter balloon using osmosis. An elongate catheter shaft has a proximally disposed osmotic membrane in fluid communication with a distally mounted balloon through a fluid-filled catheter lumen. The balloon is inflated by exposing the exterior of the membrane to a solution that is hypotonic relative to the solution within the catheter lumen. The balloon is deflated by exposing the exterior of the membrane to a solution that is hypertonic in relation to the solution within the catheter lumen.

20 Claims, 7 Drawing Sheets

BALLOON CATHETER HAVING OSMOTIC INFLATION SYSTEM

TECHNICAL FIELD

This invention relates generally to medical devices, particularly to balloon catheters, and more particularly to a system and method for inflating a catheter balloon.

BACKGROUND OF THE INVENTION

Balloon catheters require either liquid or gaseous inflation fluids and are used in a variety of medical applications such as angioplasty, embolectomy, intra-aortic balloon pumping, pulmonary capillary wedge pressure measurement, stent deployment, thermodilution cardiac output, thrombectomy, urinary drainage, and temporary vascular occlusion to prevent atheroembolization. Except for the temporary occlusion balloon, catheter balloons are conveniently inflated and deflated using manual syringes or automatic pumping apparatuses attachable to conventional fittings at the catheters' proximal ends. However, temporary occlusion balloons, and especially distal protection devices (DPDs) advantageously comprise an elongate, slender shaft that may also be used as a guidewire to direct interventional catheters to a treatment site within a patient's vasculature. While the DPD balloon is inflated distal to a treatment site to block the flow of potentially contaminated blood, another catheter can be passed over the DPD shaft proximal end and slid onto the shaft. To accomplish this maneuver, a DPD cannot use a conventional fitting at the catheter's proximal end because such fittings are too large to allow another catheter to pass over them.

Specialized inflation systems have been developed for DPDs, including several low-profile valve designs and corresponding, removable inflation apparatuses. However, current DPD inflation systems can be awkward to use, requiring that numerous steps be carried out meticulously. Therefore, it would be desirable to provide system and method for providing distal protection that overcomes the aforementioned and other disadvantages. The present system and methods advance the state of the art.

SUMMARY OF THE INVENTION

One aspect of the present invention is a system for inflating and deflating a catheter balloon using osmosis. An elongate catheter shaft has a proximally disposed semipermeable membrane in fluid communication with a distally mounted balloon through a fluid-filled lumen. The balloon is inflated by exposing the exterior of the membrane to a solution that is hypotonic relative to the solution contained in the catheter lumen. The balloon is deflated by exposing the exterior of the membrane to a solution that is hypertonic in relation to the solution contained in the catheter lumen. The system includes first and second vials, each having an opening for receiving the semipermeable membrane. The first vial contains a relatively hypotonic solution for inflating the balloon. The second vial contains a relatively hypertonic solution for deflating the balloon.

Another aspect of the present invention is a system for providing distal protection. The system includes a hypotube having a distally disposed occlusion balloon a proximally disposed, semipermeable, osmotic membrane in fluid communication with the occlusion balloon. The system further includes means for inflating the balloon.

Another aspect of the present invention is a method of using a balloon catheter. The method includes advancing a catheter balloon to a treatment site, the balloon being in fluid communication with a catheter lumen containing a first solution, inserting a semipermeable membrane located at a proximal end of the catheter into a first vial containing a second solution, and inflating the distal protection balloon.

The aforementioned and other features and advantages of the invention will become further apparent from the following detailed description of the presently preferred embodiments, read in conjunction with the accompanying drawings, which are not to scale. The detailed description and drawings are merely illustrative of the invention rather than limiting, the scope of the invention being defined by the appended claims and equivalents thereof.

BRIEF DESCRIPTION OF THE DRAWINGS

Similar reference numbers are used throughout the drawings to refer to similar parts.

DETAILED DESCRIPTION OF THE PRESENTLY PREFERRED EMBODIMENTS

Although the following description relates to balloon catheters for providing distal protection, the invention is not so limited. The concepts discussed herein may be applied to any type of balloon catheter that may be deemed suitable by those of skill in the art.

Figure 1:
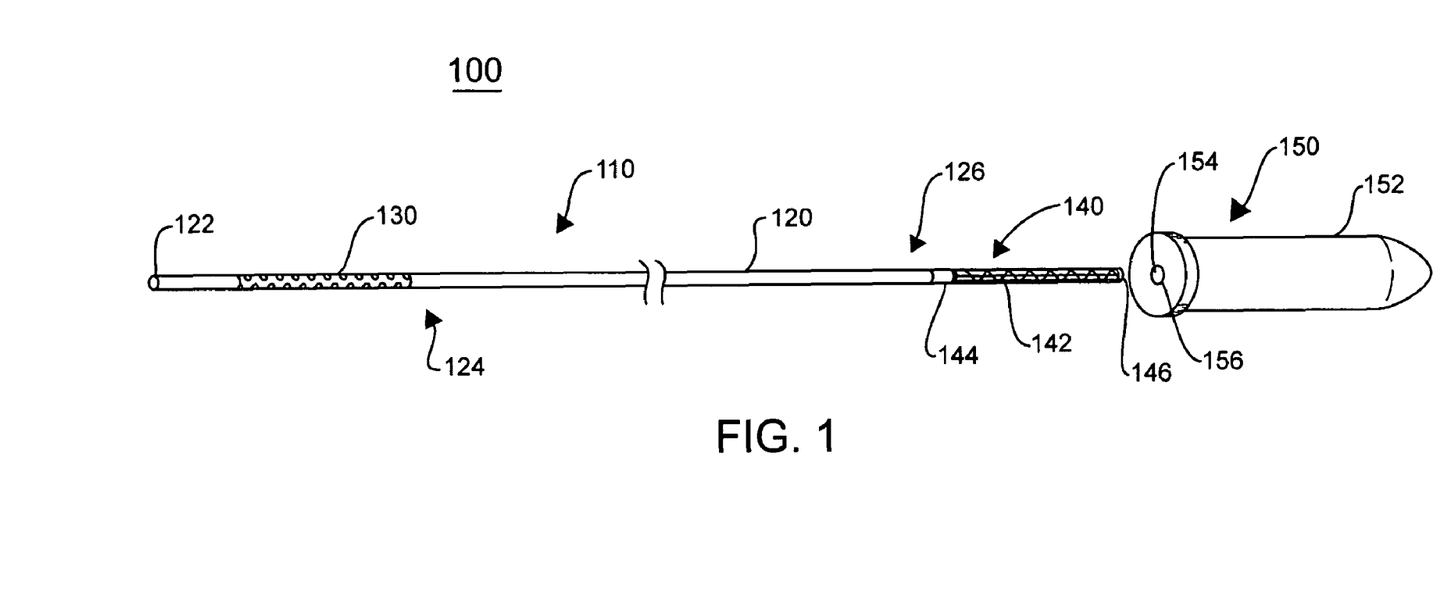
FIG. 1 is a schematic illustration of an osmotic balloon inflation system in accordance with the present invention.

FIG. 1 illustrates one embodiment of an osmotic balloon inflation system 100 for providing distal protection, in accordance with a first embodiment of the current invention. System 100 includes hypotube system 110 and osmotic solution system 150. Hypotube system 110 includes hypotube 120, balloon 130 and osmotic membrane system 140. "Hypotube" or "hypotubing," as used herein refer to thin-walled tubing similar to the tubing originally used for manufacturing hypodermic needles. For this invention, hypotubing may comprise a metal such as stainless steel, nitinol (TiNi), or work-hardenable nickel-cobalt-chromium-molybdenum superalloy, or hypotubing may comprise a high-density polymer such as thermoset polyimide.

Hypotube 120 is an elongated tube having an inner lumen for fluid communication between balloon 130 and osmotic membrane system 140. Balloon 130 communicates with the inner lumen via an inflation/deflation port (not shown) extending through the wall of the hypotubing. Hypotube 120 is sufficiently flexible to navigate the vasculature from an entry site to a location within the patient's vasculature adjacent a treatment site. In one embodiment, hypotube 120 comprises a guidewire having a lumen in fluid communication with balloon 130. Hypotube 120 includes a soft distal tip 122 for protecting the inner walls of the vasculature as the hypotube is advanced to the treatment site. The terms "distal" and "proximal" are used herein with reference to the treating clinician during deployment of the device; "distal" indicates an apparatus portion distant from, or a direction away from the clinician and "proximal" indicates an apparatus portion near to, or a direction towards the clinician.

Balloon 130 may be one of any variety of balloons or other inflatable members capable of expanding, and optionally providing distal protection. Balloon 130 may be made from flexible biocompatible materials having a wide range of elasticity. Such materials may include elastic material such as latex, silicone elastomer, or other viscous forms of natural and synthetic rubbers such as butadiene/acrylonitride copolymers, copolyesters, ethylene vinylacetate (EVA) polymers, ethylene/acrylic copolymers, ethylene/propylene copolymers, polyalkylacrylate polymers, polybutadiene, polybutylene, polyethylene, polyisobutylene, polyisoprene, polyurethane, styrenebutadiene copolymers, and styrene-ethylene/butylene-styrene, or less elastic polymers such as polyesters, polyolefins, polyamides, polyvinyl chloride, and combinations of the above. Balloon 130 is positioned near distal end 124 of hypotube 120 proximal to distal tip 122. Balloon 130 may be affixed to hypotube 120 using adhesive or any other method as is known in the art.

Osmotic membrane system 140 includes osmotic membrane 142 fixedly attached to membrane support 144. Osmotic membrane system 140 is positioned at or adjacent to hypotube proximal end 126, which is located outside of the patient's body during the catheterization procedure. Osmotic membrane system 140 may be attached to hypotube 120 by welding, soldering, adhesive or by any other means known in the art. In one embodiment, osmotic membrane system 140 is threadedly attached to hypotube 120. In another embodiment, membrane support 144 is formed integrally with hypotube 120. Osmotic membrane system 140 includes closed proximal end 146.

Osmotic membrane 142 is a semipermeable membrane that provides for the movement of a solvent from a solution of lower solute concentration to a solution of higher solute concentration. Optionally, membrane 142 may have porosity greater than the porosities of semipermeable membranes, in which case, osmosis may also drive solute particles through the membrane with the solvent. Osmotic membrane 142 may be made from a variety of materials and processes, as are particularly well known in the field of reverse osmosis equipment. Such membranes may be made of ceramic material, or of homogeneous inorganic polymer such as acrylo-nitrile, polyamide, polycarbonate, PVDF, stretched PTFE, or sulfonated polysulfone. Membrane 142 may also be a thin-film composite of inorganic polymers or organic materials, such as integrally-skinned cellulose acetate. The design of the membrane may be hollow-fiber capillary type or spirally wound type. The membrane may be formed by fission particle-irradiation, phase inversion process induced by the immersion precipitation technique, thermal or mechanical forming or a combination of these methods.

The flow through a membrane is controlled by its specific hydraulic permeability, thickness, area, transmembrane pressure, and the viscosity of the fluid passing through it. Membrane permeability is based on the sizes and number of pores that allow the solution to enter and pass through to the other side. Table 1 lists the general terminology of pores and the types of filtration processes commonly associated with various pore sizes.

TABLE 1

| Nominal Pore Size | Pore Dimensions | Uses |
|---|---|---|
| Macropore | width > 50 nm | UF, MF and filtration |
| Mesopore | 2 nm < width < 50 nm | UF, NF |
| Micropore | width < 2 nm | NF |
| Supermicropore | 0.7 nm < width < 2 nm | RO, NF |
| Ultramicropore | width < 0.7 nm | RO, GS, dialysis |
| Ultrapore | width < 0.35 nm | RO, GS, dialysis |

(Abbreviations: UF—ultrafiltration, MF—microfiltration, NF—nanofiltration, RO—reverse osmosis, GS—gas and vapor separation)

In one embodiment, osmotic membrane 142 is a rigid membrane attached to membrane support 144 and is capable of withstanding elevated pressures during inflation and deflation of balloon 130, as will be discussed in more detail below in relation to FIGS. 2-5. In another embodiment, osmotic membrane 142 is a flexible membrane rigidly supported by membrane support 144, as will be discussed in more detail below in relation to FIGS. 6-8. In the latter embodiment, membrane support 144 provides rigidity to flexible membrane 142 to allow membrane 142 to withstand the elevated pressures that occur during inflation and deflation of balloon 130.

Osmotic solution system 150 comprises vial 152 suitable for containing an osmotic fluid, which will be discussed in more detail below. The size and shape of vial 152 may vary depending on the amount of fluid to be contained as well as other factors. Vial 152 may be comprised of metal, polymeric material, or natural or synthetic rubber material or combinations thereof, such as a rigid housing surrounding an elastic bladder for containing a fluid. Vial 152 includes opening 154 for receiving at least a portion of osmotic membrane system 140. Opening 154 may have a shape complementary to the shape of osmotic membrane system 140. Opening 154 is covered or sealed by self-sealing valve 156 to prevent the leakage of osmotic fluid from vial 152 when osmotic membrane system 140 is disconnected from vial 152. Self-sealing valves are well known to those with skill in the art. Examples include various types of self-sealing valves used in catheter introducer sheaths.

Figure 2:
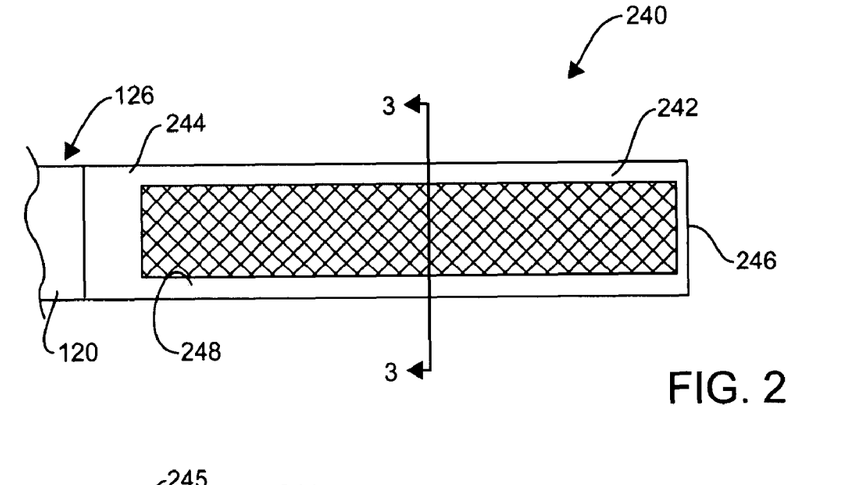
FIGS. 2 and 3 illustrate one embodiment of the osmotic inflation system shown in FIG. 1.
Figure 3:
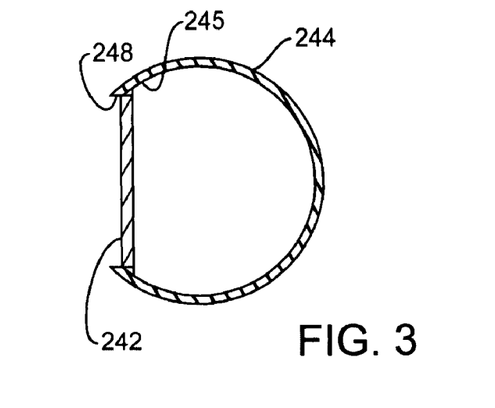

FIG. 2 is a detailed illustration of one embodiment of osmotic membrane system 240 attached to hypotube proximal end 126. FIG. 3 is a cross section of osmotic membrane system 240 taken along line 3-3 of FIG. 2. Osmotic membrane system 240 includes a rigid osmotic membrane 242 disposed within opening 248 of membrane support 244. Opening 248 may be formed by laser cutting hypotube 120. Opening 248 exposes membrane 242 to osmotic fluid and allows passage of at least a solvent through membrane 242. If membrane 242 is semipermeable, then only solvent will pass through. If membrane 242 is more porous, i.e. permeable, then solute particles may also pass through. Rigid membrane 242 is attached to an inside surface 245 of membrane support 244 adjacent to opening 248. Rigid membrane 242 may be attached to membrane support 244 by adhesive or any other means such as welding or soldering. Osmotic membrane system 240 also includes closed end 246.

Figure 4:
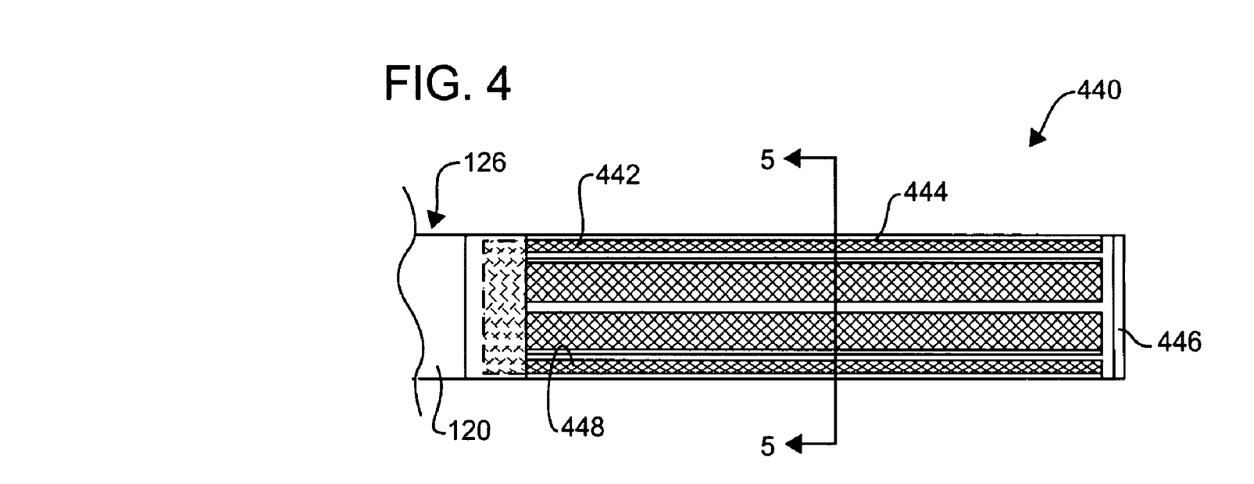
FIGS. 4 and 5 illustrate another embodiment of the osmotic inflation system shown in FIG. 1.
Figure 5:
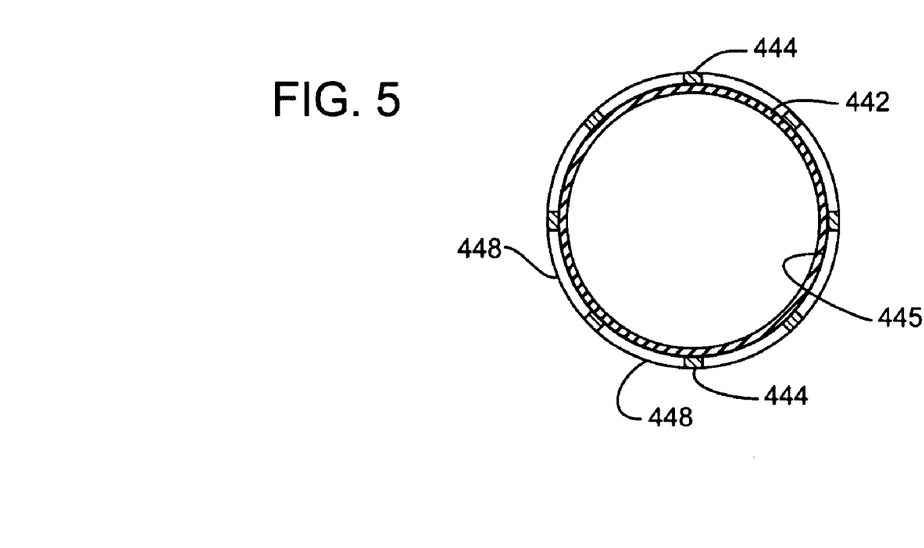

FIG. 4 is a detailed illustration of another embodiment of osmotic membrane system 440 attached to hypotube proximal end 126. FIG. 5 is a cross section of osmotic membrane system 440 taken along line 5-5 of FIG. 4. Osmotic membrane system 440 includes cylindrical, rigid membrane 442 disposed against inside surface 445 of membrane support 444. Rigid membrane 442 may be permeable or semipermeable and may be attached to inside surface 445 in a variety of ways that may be contemplated by those with skill in the art.

Membrane support 444 includes a plurality of openings 448 positioned to expose the outer surface of membrane 442 to osmotic fluid and to allow passage of at least a solvent through membrane 442. Osmotic membrane system 440 also includes closed end 446.

Figure 6:
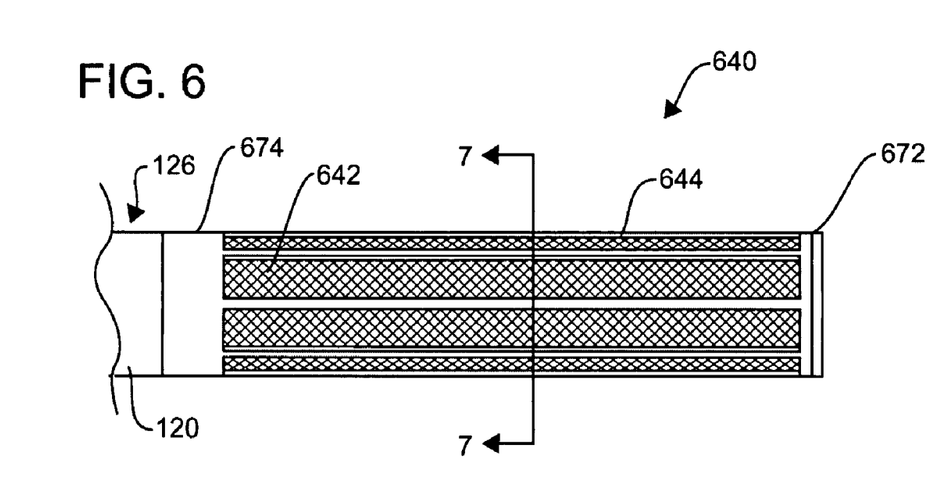
FIGS. 6 through 8 illustrate another embodiment of the osmotic inflation system shown in FIG. 1.
Figure 7:
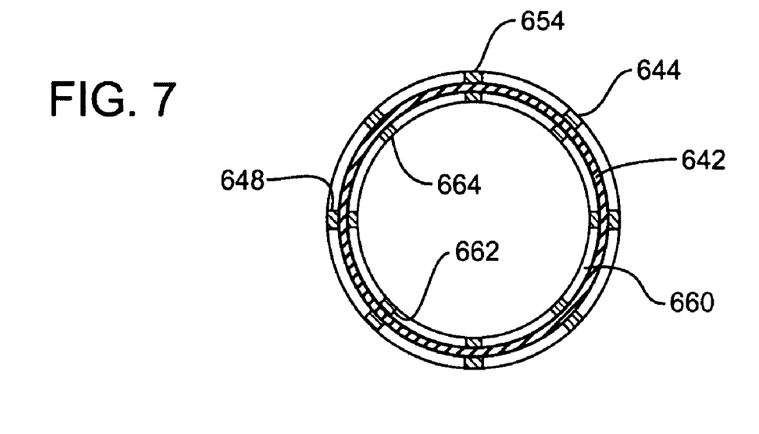
Figure 8:
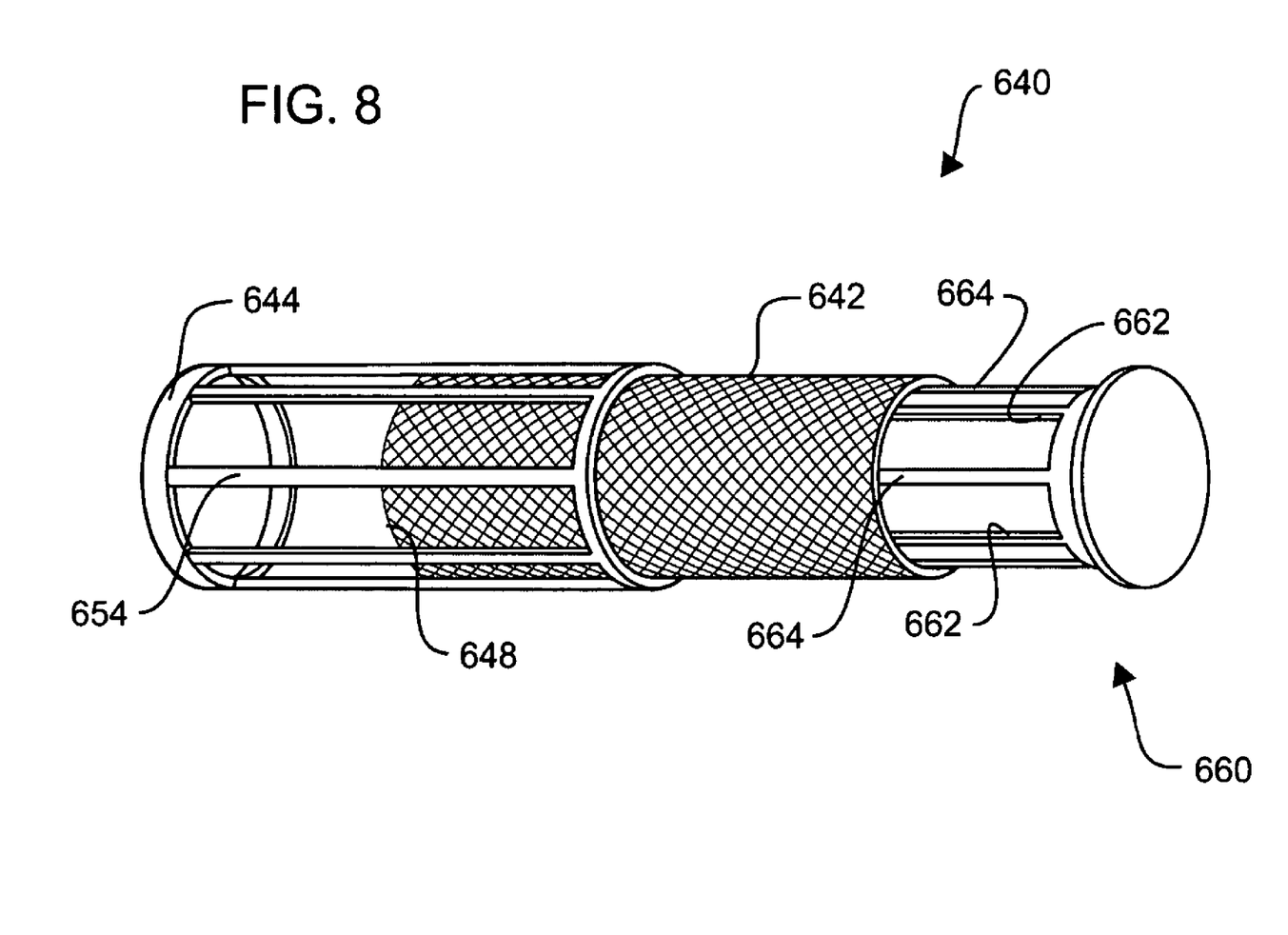

FIG. 6 is a detailed illustration of another embodiment of osmotic membrane system 640 attached to hypotube proximal end 126. FIG. 7 is a cross section of osmotic membrane system 640 taken along line 7-7 of FIG. 6. FIG. 8 is a partially exploded view of osmotic membrane system 640 shown in FIG. 6.

Flexible membrane 642 is a cylindrical permeable or semipermeable membrane positioned between outer membrane support 644 and inner membrane support 660. The arrangement of outer membrane support 644 and inner membrane support 660 provides the support necessary for membrane 644 to withstand the pressures that occur during the inflation and deflation processes, and the pressure that may be sustained within balloon 130 and the lumen of hypotube 120 during prolonged inflation times. As illustrated, outer membrane support 644 and inner membrane support 660 each provide a framework 654, 664 having openings 648, 662 that allow for the passage of at least a solvent through membrane 642. As shown in FIG. 7, framework 654 of outer membrane support 644 aligns with framework 664 of inner membrane support 660, thereby aligning the plurality of openings 648 of outer membrane support 644 with the plurality of openings 662 of inner membrane support 660.

Inner membrane support 660 may be attached to outer membrane support 644 to fixedly position membrane 642 between membrane supports 644, 660. In one embodiment, inner membrane support is welded to outer membrane support at each of proximal end 672 and distal end 674 of osmotic membrane system 640. Membrane 642 may be attached to one or both of outer membrane support 644 and inner membrane support 660. In one embodiment, membrane 642 is fixedly attached to framework 654 of outer membrane support using adhesive. In another embodiment, semipermeable membrane 642 is fixedly attached to both of framework 654 of outer membrane support and framework 664 of inner membrane support 660 using adhesive. Those with skill in the art will recognize that the arrangement and attachment of the osmotic membrane to proximal end 126 of hypotube 120 may be varied.

Figure 9:
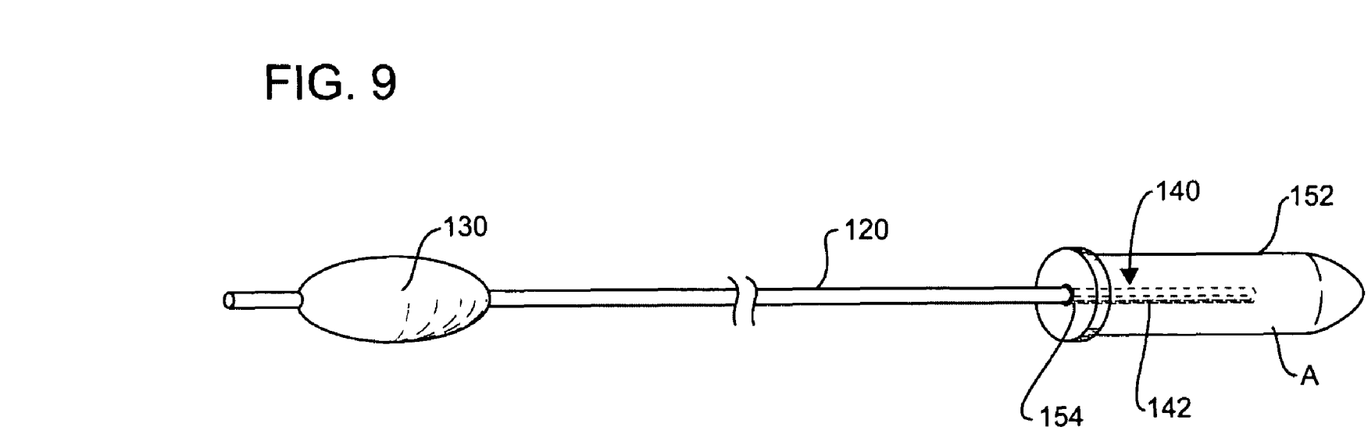
FIG. 9 is a schematic illustration showing the inflation of a balloon using the osmotic inflation system of FIG. 1.
Figure 10:
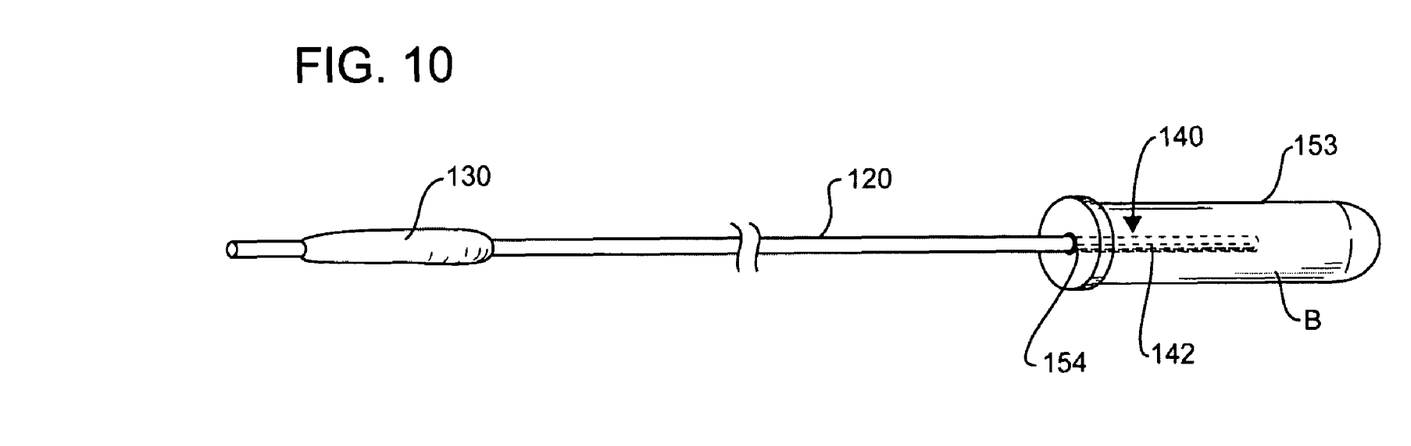
FIG. 10 is a schematic illustration showing the deflation of a balloon using the osmotic inflation system of FIG. 1.

FIGS. 9 and 10 illustrate, respectively, osmotic inflation and deflation of the catheter balloon shown in FIG. 1. Hypotube system 110 is a closed system that only allows for the movement of fluid into and out of hypotube 120 via osmotic membrane 142, which may be permeable or semipermeable. The lumen of hypotube 120 is filled with a first fluid solution. To inflate balloon 130, osmotic membrane system 140 is inserted into vial 152 through opening 154, thus exposing membrane 142 to second fluid solution "A" contained within vial 152. Solution "A" is hypotonic with respect to the first solution. By osmosis, solvent with or without solute particles, will flow from a solution with lower solute concentration, through a membrane, and into a solution with higher solute concentration, until the two solution concentrations are equilibrated. Transmembrane flow may also be stopped by the attainment of a hydrostatic or osmotic pressure on the side having higher solute concentration, or by removing one of the solutions from contact with the membrane. In this example of the invention, the solvent in solution "A" will flow from vial 152, across membrane 142, adding fluid volume to the lumen of hypotube 120. The increasing volume of fluid within hypotube 120 will expand into the interior of balloon 130.

As balloon 130 begins to resist inflation, pressure will increase in the balloon and the hypotube lumen. If the internal pressure in the catheter reaches the osmotic pressure determined by the osmolarity of the two solutions, then solvent flow and balloon inflation will stop, regardless of whether the two solution concentrations have equilibrated. When balloon 130 has been inflated to a desired volume or pressure, osmotic membrane system 140 is removed from vial 152 to halt the inflation process. As catheter 100 comprises a closed fluid system, balloon 130 will remain inflated.

To deflate balloon 130, the clinician inserts osmotic membrane system 140 into vial 153 containing third solution "B." Solution B is hypertonic as compared to the solution contained within closed hypotube 120, especially after the balloon inflation process, which reduces the concentration of the solution within hypotube 120. Exposure of membrane 142 to hypertonic solution "B" within vial 153 causes fluid to flow from the lumen of hypotube 120, across membrane 142 and into vial 153, thereby deflating balloon 130. The rate of balloon inflation or deflation will depend on the fluid flow rate across membrane 142, and this flow rate will be determined by the solution concentrations adjacent membrane 142. Because the hypotube lumen is long and slender, a solution concentration gradient will likely occur, at least initially, along the lumen from balloon 130 to osmotic membrane system 140. That is, it will take some time for concentration changes within osmotic membrane system 140 to disperse throughout the fluid within the catheter.

As those with skill in the art will understand, a myriad of solutes can be utilized in preparing osmotic solutions used to practice this invention. Solutes may be, for example, glucose, lactose, sucrose, sodium chloride, potassium chloride, glycine, albumin, insulin, combinations thereof, and the like. Sterile water is a suitable solvent, although other biocompatible solvents may be used to make inflation/deflation solutions of the invention.

In a first example of solutions used to inflate and deflate balloon 130, the solution within hypotube system 110 is a 0.5 M glucose solution, solution "A" is a relatively hypotonic 0.1 M glucose solution and solution "B" is a relatively hypertonic 1.0 M glucose solution. In a second example, the solution within hypotube system 110 is a 1 gram NaCl/liter solution, solution "A" is a relatively hypotonic 0.1 gram NaCl/liter solution and solution "B" is a relatively hypertonic 2 gram NaCl/liter solution. Those with skill in the art will recognize that the specific solutes and the concentrations of solutes may be varied to affect the inflation and deflation of balloon 130. Additionally, the design of the osmotic membrane may be varied, as discussed above, to alter the rate of fluid flow there through.

Figure 11:
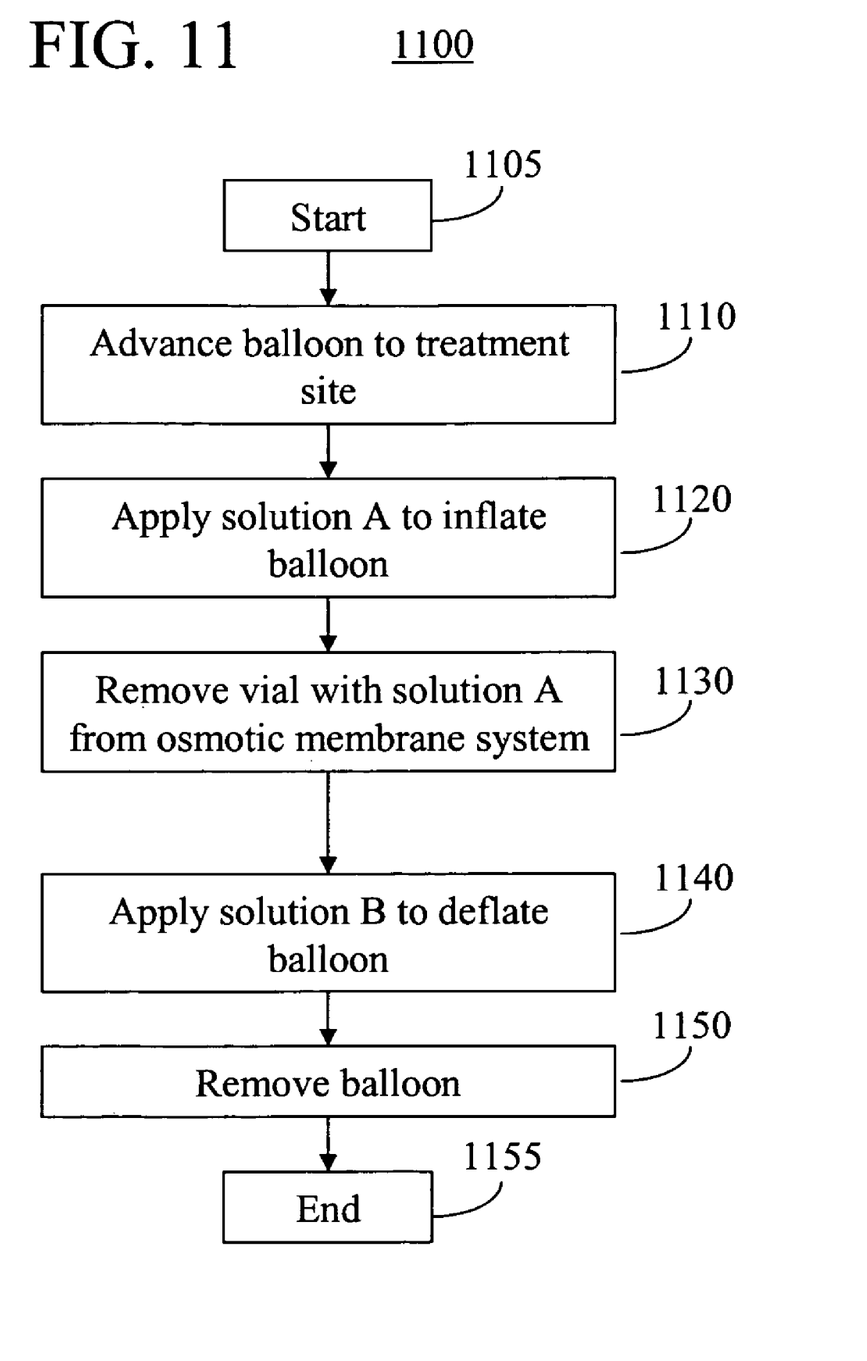
FIG. 11 is a flow diagram of one method of using an osmotic balloon inflation system, in accordance with the present invention.

Another aspect of the present invention is a method of using a balloon catheter having an osmotic inflation system. FIG. 11 shows a flow diagram of one embodiment of method 1100 in accordance with the present invention. Method 1100 begins at block 1105. Catheter balloon 130 is advanced through the patient's vasculature to the treatment site (Block 1110). The advancement and positioning of the catheter and balloon 130 may be visualized by any method known to those with skill in the art. In one embodiment, the catheter system includes radiopaque markers to aid in fluoroscopic visualization of the system as it traverses the vasculature.

Once balloon 130 is in a desired position, balloon 130 is inflated by inserting osmotic membrane system 140 into vial 152 containing second solution "A," which is hypotonic relative to a first solution contained in a balloon inflation lumen of the catheter (Block 1120). Fluid from solution "A" flows through osmotic membrane 142 into the catheter lumen as described above. The clinician may monitor the inflation of balloon 130 and, upon achieving the desired size or pressure of inflation, the clinician may remove vial 152 from the osmotic membrane system 140 (Block 1130).

Alternatively, the osmotic inflation system may be designed such that the desired size or pressure of balloon inflation is achieved upon equilibration of concentrations of the first and second solutions, or when the pressure within the balloon reaches osmotic pressure. In either of these embodiments, removal of vial 152 is unnecessary to stop inflation when balloon 130 reaches the desired configuration.

Upon completion of the procedure or at any other time the clinician desires to deflate balloon 130, the clinician inserts osmotic membrane system 140 into vial 153 containing solution "B," which is hypertonic relative to the solution contained in the balloon inflation lumen of the catheter (Block 1140). Fluid from the catheter lumen flows through membrane 142 into vial 153. After balloon 130 deflates, the catheter may be removed from the patient (Block 1150).

In other embodiments, hypotube system 110 may be used as a guidewire to advance catheters and the like to the treatment site after the distal balloon is positioned and inflated. In such embodiments, simply removing vial 152 from osmotic membrane system 140 completes the balloon inflation process and leaves the hypotube proximal end without any connector fitting or other impediment to loading a catheter over the hypotube.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A system comprising:
   an elongate hollow shaft having a lumen filled with a first fluid solution, the shaft having an outer diameter sized to act as a guidewire;
   a balloon disposed adjacent a distal end of the shaft and in fluid communication with the lumen;
   an osmotic membrane disposed adjacent a proximal end of the shaft and in fluid communication with the lumen, wherein the proximal end of the shaft having the osmotic membrane is sized for insertion into a guidewire lumen of a treatment catheter; and
   a first vial having a first vial opening configured to removably receive the osmotic membrane through the first vial opening into the first vial, the first vial containing a second fluid solution different from the first fluid solution.

2. The system of claim 1 wherein the second solution is hypotonic relative to the first solution.

3. The system of claim 2 further comprising:
   a second vial different from the first vial containing a third fluid solution different from the second fluid solution, the second vial having a second vial opening configured to removably receive the osmotic membrane through the second vial opening into the second vial.

4. The system of claim 3 wherein the third solution is hypertonic relative to the second solution.

5. The system of claim 3 wherein the first solution, the second solution and the third solution each contain a solute chosen from the group consisting of glucose, lactose, sucrose, sodium chloride, potassium chloride, glycine, albumin, insulin, and combinations thereof.

6. The system of claim 3 wherein the first solution comprises a 0.5 M glucose solution, the second solution comprises a 0.1 M glucose solution and the third solution comprises a 1.0 M glucose solution.

7. The system of claim 3 wherein the first solution comprises a 1 gram NaCl/liter solution, the second solution comprises a 0.1 gram NaCl/liter solution and the third solution comprises a 2 gram NaCl/liter solution.

8. The system of claim 1 wherein the osmotic membrane is a semipermeable membrane.

9. The system of claim 1 wherein the osmotic membrane is a rigid membrane.

10. The system of claim 1 wherein the osmotic membrane is a flexible membrane.

11. The system of claim 1 further comprising a membrane support fixedly attached adjacent the proximal end of the shaft.

12. The system of claim 11 wherein the membrane support comprises an outer membrane support and an inner membrane support, the osmotic membrane being disposed there between.

13. The system of claim 11 wherein the membrane support comprises a framework having a plurality of openings.

14. The system of claim 1 wherein the elongate hollow shaft is a guidewire.

15. A method of using a balloon catheter, the method comprising:
   providing the balloon catheter comprising:
      an elongate hollow shaft having a catheter lumen, the shaft sized for insertion into a guide wire lumen of a treatment catheter;
      a catheter balloon disposed adjacent a distal end of the shaft, the balloon in fluid communication with the catheter lumen containing a first solution; and
      an osmotic membrane disposed adjacent a proximal end of the shaft and in fluid communication with the catheter lumen;
   advancing the catheter balloon to a treatment site in a patient; and
   inserting the osmotic into a first vial containing a second solution different from the first solution, thereby inflating the balloon, the first vial having an opening configured to removably receive the osmotic membrane through the opening.

16. The method of claim 15 further comprising:
   deflating the balloon.

17. The method of 16 wherein deflating the balloon comprises:
   inserting the membrane into a second vial different from the first vial containing a third solution different from the second solution.

18. The method of claim 17 wherein the third solution is hypertonic relative to the second solution.

19. The method of claim 15 wherein the second solution is hypotonic relative to the first solution.

20. The method of claim 15 further comprising:
   removing the osmotic membrane from the first vial based on the inflation of the balloon;
   inserting the proximal end having the osmotic membrane into a lumen of the treatment catheter; and
   advancing the treatment catheter over the proximal end of the shaft and in a distal direction toward the inflated balloon at the treatment site.

* * * * *